United States Patent
Daly et al.

(10) Patent No.: US 6,346,104 B2
(45) Date of Patent: *Feb. 12, 2002

(54) SYSTEM FOR SIMULTANEOUS UNIPOLAR MULTI-ELECTRODE ABLATION

(75) Inventors: Michael Daly, Eastwood; Pramesh Kovoor, Wentworthville; Konstadinos Hatzianestis, McMahons Point; David Ross, Cheltenham, all of (AU)

(73) Assignee: Western Sydney Area Health Service, New South Wales (AU)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/952,175

(22) PCT Filed: Apr. 30, 1997

(86) PCT No.: PCT/AU97/00258

§ 371 Date: Jan. 22, 1998

§ 102(e) Date: Jan. 22, 1998

(87) PCT Pub. No.: WO97/40760

PCT Pub. Date: Nov. 6, 1997

(30) Foreign Application Priority Data

Apr. 30, 1996 (AU) .............................................. PN9572

(51) Int. Cl.[7] .............................................. A61B 18/14
(52) U.S. Cl. .............................. 606/34; 606/41; 607/99
(58) Field of Search .............................. 606/34, 41, 49; 607/99, 119, 122

(56) References Cited

U.S. PATENT DOCUMENTS

| 4,182,996 | A | | 1/1980 | Spence ........................ 333/100 |
|---|---|---|---|---|
| 5,023,945 | A | | 6/1991 | Childs ........................ 455/617 |
| 5,334,193 | A | * | 8/1994 | Nardella ........................ 606/41 |
| 5,403,311 | A | * | 4/1995 | Abele et al. .................... 606/49 |
| 5,496,312 | A | * | 3/1996 | Klicek ........................ 606/34 |
| 5,540,681 | A | | 7/1996 | Strul et al. .................... 606/34 |
| 5,630,426 | A | * | 5/1997 | Eggers et al. .................. 606/34 |
| 5,810,802 | A | * | 9/1998 | Panescu et al. ................ 606/41 |

FOREIGN PATENT DOCUMENTS

| WO | 8301902 | 6/1983 |
|---|---|---|
| WO | 9300958 | 1/1993 |
| WO | 9423794 | 10/1994 |
| WO | 9525472 | 9/1995 |
| WO | 9629946 | 10/1996 |
| WO | 9706727 | 2/1997 |

* cited by examiner

Primary Examiner—Lee Cohen
(74) Attorney, Agent, or Firm—Ladas & Parry (57) ABSTRACT

A system (2,4), method and splitter (6) for ablating tissue (15) using radiofrequency (RF) energy is disclosed. The system (2,4) ablates tissue (15) using unipolar RF energy simultaneously delivered to multiple electrodes (22A–22D) in one or more probes (20). This is carried out by the multiple channel RF splitter (6) that can independently control the RP energy delivered through each channel (18) to a respective electrode (22A–22D) in a continuous manner. Each electrode (22A–22D) has a corresponding temperature sensor or transducer (36A–36D) that is processed independently so that the amount of RF energy delivered to each electrode (22A–22D) can be varied dependent on the temperature of the electrode (22A–22D) so that the lesion size produced by each electrode (22A–22D) can be accurately controlled. Preferably, each probe (20) has a needle-like structure with a number of electrodes (22A–22D) separated by insulative material and is adapted to puncture tissue. Each channel (18) of the splitter (6) has circuitry for interrupting current delivered to the respective channel if a predetermined temperature or current level is exceeded.

32 Claims, 4 Drawing Sheets

SYSTEM FOR SIMULTANEOUS UNIPOLAR MULTI-ELECTRODE ABLATION

BACKGROUND

The present invention relates to a system, method and apparatus for ablating tissue under temperature control of each electrode to control lesion dimensions, and in particular for ablating myocardial tissue to treat Ventricular Tachycardia (VT) or atrial fibrillation/flutter (AF).

Ventricular tachycardia is a disease of the heart which causes the heart chambers to beat excessively fast and usually degenerates to ventricular fibrillation where the heart chambers do not effectively pump blood through the body's system and hence leads to death. Ventricular tachycardia is the most common cause of cardiac arrest and sudden death. Typical features of patients with VT are (1) a history of myocardial infarction (heart attack), (2) significant left ventricular dysfunction (the main chamber effecting the pumping action), and (3) left ventricular aneurysm (dilation, thinning and stretching of the chamber). Detailed mapping studies of the electrical propagation within the myocardium during VT have shown that a re entrant pathway within and around the scarring (caused by infarction) is responsible for the arrhythmia, These studies have shown that the critical area of myocardium necessary to support reentry appears to be less than 2 to 4 $cm^2$.

Atrial fribillation (AF) and atrial flutter are diseases of the heart which can cause the heart to beat excessively fast and frequently in an erratic manner. This usually results in distress for patients. This may also be associated with clot formation in the atria, which may become dislodged and cause strokes. AF is usually due to abnormal electrical activation of the atria. Preliminary investigations have shown that linear lesions in the atria using radiofrequency ablation can cure these arrhythmias.

A number of conventional techniques using radio frequency (RF) energy have been used to treat VT or AF. Endocardial radio frequency catheter ablation has been used in the treatment of hemodynamically stable monomorphic ventricular tachycardia secondary to coronary artery disease. The resulting lesions caused in RF ablation using catheters however have been insufficient in volume to destroy the area of tissue causing the arrhythmia.

Radiofrequency catheter ablation on has been used for treatment of AF but has been limited by the number of separate ablationis required and the time required to perform the procedure.

In accordance with one conventional technique, RF energy is delivered from an RF source, incorporating phase shift networks to enable potential differences and hence current flow between multiple, separate electrode structures Also, multiple RF power sources have been used connected to such electrodes. The independent phases of the power source lead to multiple current paths.

However, this conventional system lacks adequate temperature cntrol because the multiphase RF ablation cannot function satisfactorily unless certain restrictions on the dimensions of the electrode are adhered to. The ablation temperature can only be maintained at an optimum predetermined level of approximately 80° C. This is a significant shortfall of the technique.

SUMMARY

The present invention is directed to improving the efficacy of producing radio frequency lesions using multiple temperature controlled delivery by splitting high frequency current from a single generator into a number of electrodes simultaneously. Further, the system accurately measures the temperatures of these electrodes which are then used as the feedback in the system, allowing appropriate control strategies to be performed to regulate the current to each electrode.

In accordance with a first aspect of the invention, a system for ablating tissue comprises:
- a device for generating RF energy;
- a probe device comprising N separate electrodes, each having a corresponding device for sensing the temperature of the electrode;
- a splitter device for splitting the RF energy coupled to the generating device and the probe device, the splitter device having N separate channels each being coupled to a corresponding one of the N electrodes and temperature sensing device; and
- a device for controlling the splitter device, whereby the ablation of tissue at each electrode is independently controlled using closed loop feedback of the temperature of the electrode by independently regulating the amount of the RF energy delivered to each electrode.

Preferably, the system comprises a plurality of the probe devices and the splitter devices, and the controlling device separately controls each of the probe devices and the corresponding splitter device.

Preferably, the probe device has an elongated needle-like structure with one end adapted to puncture tissue and having sufficient rigidity to puncture the tissue, or a catheter which can be advanced into the heart. Each of the electrodes may consist of a circular metal surface separated one from another by insulation.

Preferably, the RF energy has a single phase.

Preferably, the system further comprises a device for independently and continuously adjusting the RF energy delivered to each electrode in response to a control signal from the controlling device dependent on the temperature of the electrode.

Preferably, the controlling device is programmable.

Optionally, the probe device is a catheter probe device.

Preferably, each of the temperature sensing devices is a thermocouple. Preferably, the splitter device comprises one or more devices for independently interrupting current from the RF energy generating device to a respective electrode.

In accordance with a second aspect of the invention, a medical apparatus for treatment by radiofrequency ablation of tissue comprises:
- an RF energy generator;
- one or more probes each comprising a plurality of separate electrodes and corresponding temperature sensors for sensing the termperature of the electrodes, each temperature sensor connected to a respective one of the plurality of electrodes;
- a splitter for splitting the RF energy provided by the RF energy generator, the splitter having a plurality of separate channels, wherein each of the electrodes is coupled to a respective one of the plurality of channels; and
- a programmable controller coupled to the RF splitter for independently controlling the ablation of tissue at each electrode using closed loop feedback of the temperature of the electrode, whereby the amount of the RF energy delivered to each electrode is independently regulated by the programmable controller.

In accordance with a third aspect of the invention, a radio frequency energy splitter for use with one or more probes in a system for RF ablation of tissue is provided. Each probe comprises a plurality of separate electrodes and corresponding temperature sensors for sensing the temperature of the electrode. The splitter comprises:

an input device for receiving RF energy from an RF energy generator;

a plurality of channel modules for separately delivering RP energy from the input device to a respective electrode of the plurality of electrodes of the one or more probes, each channel module comprising:

a device for variably adjusting an amount of the RF energy delivered to the respective electrode in response to a control signal, the variable adjusting device being coupled between the input device and the respective electrode;

a device for interrupting the RF energy delivered to the respective electrode;

an output device coupled to the respective temperature sensor for providing a temperature signal;

a device for determining if the temperature at the respective electrode exceeds a predetermined threshold and actuating the interrupting device if the threshold is exceeded, whereby the RF energy is interrupted from delivery to the respective electrode;

wherein each channel module is capable of receiving the respective control signal from and providing the respective temperature signal to a programmable controller so that the amount of the RF energy delivered to each electrode can be independently regulated using closed loop feedback of the temperature of each electrode.

Preferably, the variable adjusting device or circuit comprises a bridge rectifier including a fast-switching variable resistance for controlling operation of the bridge rectifier in response to the control signal.

Preferably, the RF energy interrupting device comprises a circuit for interrupting a current through the RF energy interrupting device and a circuit for limiting the current.

Preferably, the determining device compares the temperature signal with the predetermined threshold.

In accordance with a fourth aspect of the invention, a method for ablating tissue comprises the steps of:

generating RF energy;

providing a probe device comprising N separate electrodes, each having a corresponding temperature sensing device;

measuring the temperature of each electrode using the temperature sensing device of the electrode;

splitting the RF energy to the probe device into N separate channels each being coupled to a corresponding one of the N electrodes and temperature sensing device; and controlling the splitting of the RF energy to the probe device, whereby the ablation of tissue at each electrode is independently controlled using closed loop feedback of the measured temperature of the electrode by independently regulating the amount of the RF energy delivered to each electrode.

Preferably, the method comprises the step of separately controlling the splitting of the RF energy to a plurality of the probe device.

Preferably, the probe device has, an elongated needle-like structure with one end adapted to puncture tissue and having sufficient rigidity to puncture the tissue, wherein each of the electrodes consists of a metal substantially circular surface separated one from another by insulation.

Preferably, the RF energy has a single phase.

Preferably, the method further comprises the step of independently and continuously adjusting the RF energy delivered to each electrode in response to a control signal from a programmable controlling device dependent on the temperature of the electrode.

In accordance with a fifth aspect of the invention, a method for treatment by radiofrequency (RF) ablation of tissue comprises the steps of:

generating RF energy;

providing one or more probes each comprising a plurality of separate electrodes and corresponding temperature sensors, each temperature sensor connected to a respective one of the plurality of electrodes;

measuring the temperature of each electrode using the respective temperature sensor;

splitting the RF energy into a plurality of separate channels, wherein each of the electrodes is coupled to a respective one of the plurality of channels; and programmably controlling the splitting of the RF energy so as to independently control the ablation of tissue at each electrode using closed loop feedback of the measured temperature of the electrode. whereby the amount of the RF energy delivered to each electrode is independently regulated Preferably, the method involves using at least two probes, and comprises the step of programmably controlling each of the probes separately.

In accordance with a sixth aspect of the invention, there is provided a method of splitting radio frequency energy delivered to one or more probes in a system for RF ablation of tissue. Each probe comprises a plurality of separate electrodes and corresponding temperature sensors for sensing the temperature of the electrode. The method comprises the steps of:

receiving RF energy from an RF energy generator;

providing a plurality of channel modules for separately delivering the RF energy to a respective electrode of the plurality of electrodes of the one or more probes, further comprising, for each channel module, the substeps of:

variably adjusting an amount of the RF energy delivered to the respective electrode in response to a control signal;

measuring the temperature of the respective electrode using the corresponding temperature sensor to provide a temperature signal;

determining if the temperature at the respective electrode exceeds a predetermined threshold and interrupting delivery of the RF energy to the respective electrode if the threshold is exceeded;

wherein each channel module is capable of receiving the respective control signal from and providing the respective temperature signal to a programmable controller so that the amount of the RF energy delivered to each electrode can be independently regulated using closed loop feedback of the temperature of each electrode.

Preferably, the step of variably adjusting the RF energy comprises the step of changing the resistance of a fast-switching variable resistance incorporated in a bridge rectifier in response to the control signal.

Preferably, the step of interrupting the RP energy comprises the steps of interrupting a current to the respective electrode and limiting the current.

Preferably, the step of determining comprises the step of comparing the temperature signal with the predetermined threshold.

BRIEF DESCRIPTION OF THE DRAWINGS

Embodiments of the invention are described hereinafter with reference to the drawings, in which.

DETAILED DESCRIPTION

First Embodiment

Figure 1:
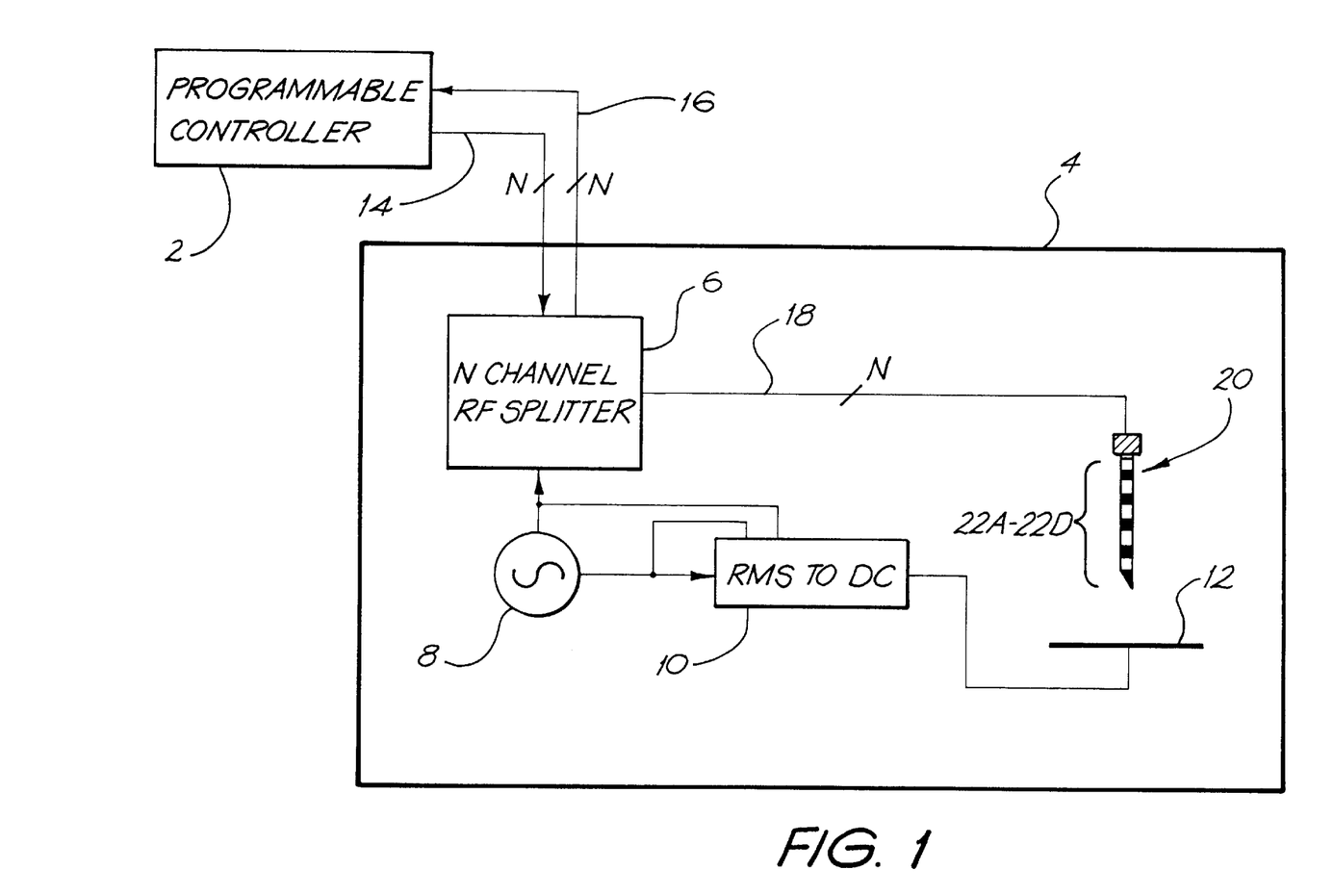
FIG. 1 is a block diagram of the RF ablation system according to one embodiment.

The RF ablating system according to a first embodiment shown in FIG. 1 comprises a programmable controller 2, an N-channel RF splitter 6, an RF generator 8, a large conductive, dispersive plate 12, and an N-electrode probe 20. RF generators for RF ablation of tissue are well known in the art. It will be appreciated by a person skilled in the art that the present invention can be practiced with any of a number of RF generators without departing from the scope and spirit of the invention.

Preferably, the probe 20 has a needle-like structure wherein each of the electrodes 22A to 22D has a tubular or ring shape. The electrodes 22A to 22D are separated from each other by an intervening insulative portion. Such a probe structure is disclosed in International Publication No. WO 97/06727 published on Feb. 27 1997 (International Application No. PCT/AU96/00489 by the Applicant) and incorporated herein by cross-reference. The structure of this probe 20 enables the electrodes 22A to 22D to be inserted into the myocardium for use in the present system. While this embodiment is described with reference to a single needle probe 20, the system may be practiced with a plurality of such needle probes 20 and one or more corresponding N-channel RF splitters 6 that are controlled by the programmable controller 2. It will be apparent to a person skilled in the art that the embodiment is not limited to the use of such needle-like probes but may be practiced with other types of ablating probes including catheters.

Further, while this embodiment is discussed with reference to ablation of reentrant pathways in relation to ventricular tachycardia, the system is not limited to this particular application, and instead can practiced in relation to a number of other applications. For example, the system may be used to ablate tissue causing atrial fibrillation or flutter, tumors, or for coagulation treatment.

The programmable controller 2 may be implemented using a general purpose computer executing a control algorithm to operate the RF splitter 6 in response to measured temperatures of the electrodes 22A to 22D, as described below. In this embodiment, the programmable controller 2 is preferably implemented using an AMLAB instrument emulator (published in International Publication No. WO92/15959 on Sep. 17, 1992; International Application No. PCT/AU92/00076), which comprises a general purpose computer having a digital signal processor subassembly that is configurable using a graphical compiler. The programmable controller 2 is connected to the N-channel RF splitter 6 via N output control signals 14 and N temperature signals 16 provided from the N-channel RF splitter 6 to the programmable controller 2. The N-channel RF splitter 6, the RF generator 8, the RMS-to-DC converter 10, the probe 20, and the dispersive plate 12, shown as module 4, are provided SO as to meet electrical isolation barrier requirements in accordance with IEC 601 and AS3200.1 type CF standards.

The N-channel RF splitter 6 provides RF energy from the RF generator 8 coupled to the splitter 6 via N electrical connections 18 to the corresponding electrodes 22A to 22D of the probe 20. In addition, the N electrical connections 18 are connected to corresponding thermocouples of each of the electrodes 22A to 22D. While thermocouples are preferably employed, other temperature transducers or sensing circuits/devices may be practiced without departing from the scope and spirit of the invention. For example, a temperature sensing device for a respective electrode of one or more electrodes could include a thermistor or other temperature transducer. The N temperature signals 16 provided to the programmable controller 2 are obtained from the temperature sensing devices of the electrodes 22A to 22D. The RF generator 8 is also connected to the dispersive electrode 12 via the RMS-to-DC converter 10.

This embodiment advantageously employs a single RF generator in which the N-channel RF splitter 6 independently controls the delivery of RF energy of a single phase to one or more of the electrodes 22A to 22D of the probe 20, The temperature of each of the electrodes 22A to 22D is independently monitored by the programmable controller 2, which in turn provides the control signals 14 to the N-channel RF splitter 6 to simultaneously control the amount of RF energy delivered to the corresponding electrode 22A to 22D.

Using closed-loop feedback and independent, simultaneous control of each electrode, the system is able to advantageously regulate temperatures to occur at each electrode at the desired temperature. This produces optimum lesion size, and avoids charring and vaporisation associated with temperatures greater than 100° C. This is in marked contrast to the prior art, since the embodiment provides a margin of at least 20° C., highlighting the lack of temperature control of all of the electrodes in the conventional system. The prior art is able to affect only the temperature of the electrode being monitored. As lesion size is proportional to the temperature of the electrodes, the system according to this embodiment is able to controllably produce larger lesions. The ability to maintain all electrodes at a desired temperature simultaneously and independently enables contiguous uniform lesions, not as dependent on the size and contact area of each electrode. Conversely, if it is desired to deliver RF energy to only one particular electrode to minimise thermal damage to "good" tissue, the system according to this embodiment is able to ensure that adjacent electrodes have minimal current. That is, the system according to this embodiment has the ability to ensure precise temperature control of each electrode individually and simultaneously.

Figure 2:
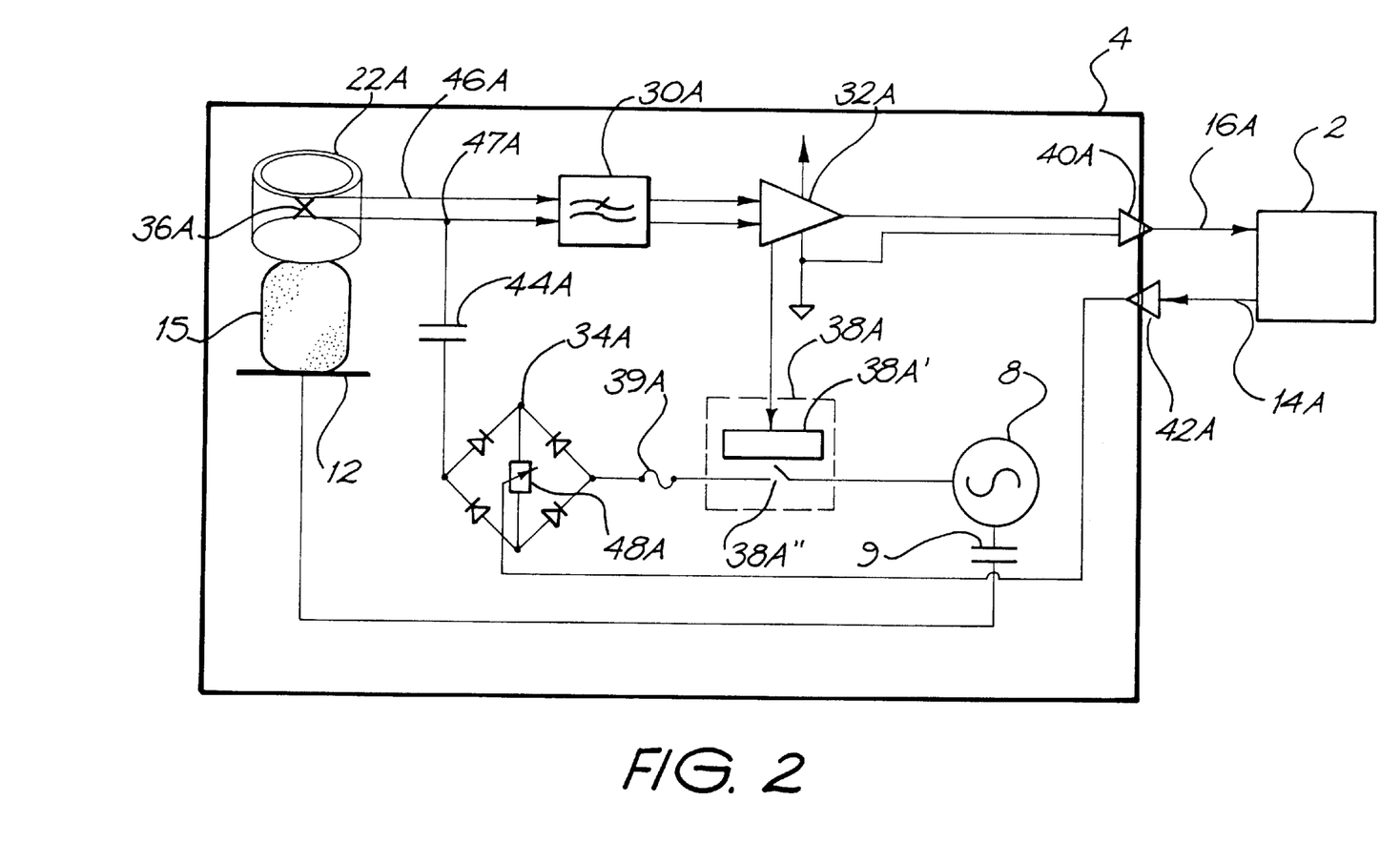
FIG. 2 is a detailed schematic of a single channel of the system of FIG. 1.
Figure 3:
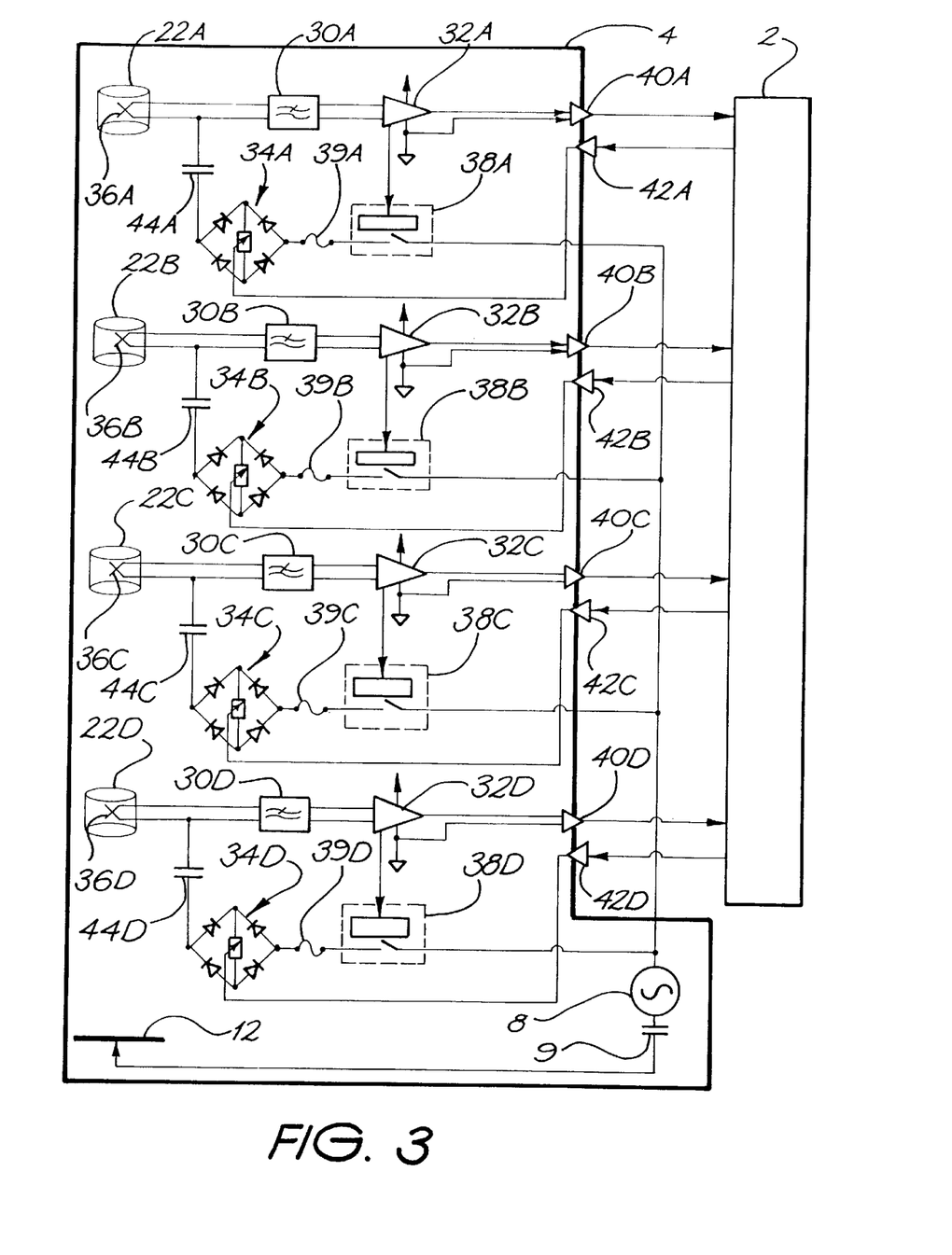
FIG. 3 is a detailed schematic of the system of FIG. 1, wherein N=4.

FIG. 3 is a detailed schematic diagram of the system of FIG. 1. As shown in FIG. 3, the number of electrodes and separate channels N is preferably four (4). However, this embodiment may be practiced with a different number (e.g., N=3 or N=5) of electrodes and channels without departing from the scope and spirit of the present invention. Further, the splitter may be practiced with N channels and a number of separate probes where the total number of electrodes of the probes is less than or equal to N. A single electrode 22A and corresponding channel of the N-channel RF splitter 6 is described hereinafter with reference to FIG. 2. While a single electrode 22A and corresponding channel are described, it will be apparent to a person skilled in the art that the following description applies equally to the three remaining electrodes 22B to 22D and the corresponding channels of the splitter of FIG. 3.

In FIG. 2, the control signal 14A output by the programmable controller 2 is provided to an isolation amplifier 42A which in turn is connected to a fast-switching, full bridge rectifier 34A. In particular! the output of the isolation amplifier 42A is connected to a fast-switching variable resistance 48A used to control operation of the rectifier bridge 34A. Preferably, the variable resistance 48A is implemented using a power N-channel enhancement MOSFET. The programmable controller 2 receives a temperature signal 16A from the output of another isolation amplifier 40A.

One terminal of the RF generator 8 is coupled via a decoupling capacitor 9 to the dispersive electrode 12. The tissue (e.g., myocardium) which the probe 20 is to be applied to is generally represented by a block 15 between the dispersive plate 12 and an electrode 22A of the needle probe 20. In this embodiment, the needle probe is inserted into the tissue. The electrode 22A is generally represented by a tubular or ring-like structure in accordance with the electrode structure employed in the needle probe 20. However, again it will be appreciated that other electrode structures may be practised dependent on the probe type without departing from the scope and spirit of the invention The other terminal of the RF generator 8 is connected via a fail-safe relay 38A and a thermal fuse, current limiter 39A to the rectifier bridge 34A. The relay 38A consists of a fail-safe relay contact 38A' and a fail-safe relay winding 38A". These circuits act as current interrupting and current limiting devices.

The output terminal of the fast-switching, fall bridge rectifier 34A is coupled via a decoupling impedance matching capacitor 44A to a stainless steel conductor 47A, which is connected to the stainless steel electrode 22A and a terminal of the thermocouple junction 36A. The stainless steel conductor 47A is also connected to a low pass filter 30A, preferably composed of passive elements. A titanium conductor 46A is also coupled to the stainless steel electrode 22A and the other terminal of the thermocouple junction 36A embedded in the electrode 22A. The titanium conductor 46A is further connected to the low-pass filter 30A. However, other conductive materials may be used for the electrode 22A and the conductors 46A and 4?A without departing from the scope and spirit of the invention. The output of the low pass filter 30A is provided to a thermocouple reference compensation amplifier and alarm 32A. The amplifier 32A also provides a control signal to the relay 38A The output of the amplifier 32A is provided to the isolation amplifier 40A, which in turn provides the temperature signal 16A to the programmable controller 2. Again, other temperature sensing devices and corresponding associated circuits to provide equivalent functionality may be practiced without departing from the scope and spirit of the invention.

The thermocouple 36A embedded in the electrode 22A produces a temperature signal on conductors 46A and 47A in response to the heat produced by the delivery of RF energy to the myocardium tissue 15. The signal produced by the thermocouple junction 36A is low-pass filtered using the low-pass filter 30A, the output of which is provided to the amplifier and alarm 32A. The alarm and amplifier 32A produces an amplified temperature signal that is provided to the isolation amplifier 40A. In addition, the amplifier and alarm 32A provides a control signal to operate the relay 38A so as to interrupt the delivery of RF energy from the RF generator via the relay 38A when the measured or sensed temperature exceeds a predetermined threshold level.

The programmable controller 2 uses the temperature signal 16A to produce a control signal 14A that is provided to the variable resistance 48A of the fill bridge rectifier 34A. This control signal 14A is provided via the isolation amplifier 42A. The control signal 14A operates the fill bridge rectifier so as to variably and continuously control the amount of RF energy delivered to the stainless steel electrode 22A for ablation. Thus, this embodiment is able to precisely and independently control the electrodes 22A to 22D of the needle probe 20.

The heating in RF energy transfer occurs not from the electrode 22A to 22D itself but from a small volume of tissue in contact with the electrode 22A to 22D, This heating source is directly proportional to the electrode surface area in contact with the tissue, contact pressure and the electrical conductivity of the tissue. Therefore, the system according to this embodiment advantageously controls the RF energy in each electrode independently of each other.

Thus, the system provides maximum control at each electrode 22A to 22D by minimising current flow between adjacent electrodes 22A to 22D. This is achieved by a single RF source (one phase) 8 using RF splitter 6 to regulate current flow to each electrode 22A to 22D as a function of the temperature of each electrode.

The first embodiment illustrated in FIGS. 1 to 3 provides a system for simultaneous unipolar, multi-electrode ablation using simultaneous closed-loop control of temperature at each electrode 22A to 22D. This system advantageously enables multi-electrode ablation for ablating ventricular tachycardia and atrial fibrillation. In contrast to conventional ablation systems which cut off current to any electrode during ablation if a temperature or impedance goes above a particular level and therefore cannot produce reliable lesions because the electrode-tissue interface surface area varies considerably during ablation, this embodiment is able to overcome this disadvantage of conventional systems. In this embodiment, the control algorithm for generating the control signals and operating the system in response to the temperature of each of the electrodes is preferably implemented in software carried out using a general purpose computer.

An experimental example of the use of the system is set forth below outlining the use of another system in accordance with that of this embodiment.

EXAMPLE

A system in accordance with the first embodiment was implemented and tested to compare unipolar versus bipolar ablation and single electrode temperature control versus simultaneous multi-electrode temperature control during ablation.

Two types of 21 gauge needles, each with 2 cylindrical electrodes were introduced from the epicardium at thoracotomy in 3 greyhounds. The proximal electrode measured 1 mm. The distal electrode measured 1 mm in one needle and 1.5 mm in the other. The inter electrode distance was 4 mm. Seventy four intramural RF ablations were performed for 60 seconds through both the electrodes of each needle simultaneously in an unipolar (Uni) or a bipolar (Bi) fashion. During ablations the temperature of only one electrode (proximal or distal) or both the electrodes simultaneously were maintained at 80° C. by closed loop control. Lesion sizes were measured histologically.

The maximum ± SD temperature (temp) measured at the proximal (P) and the distal (D) electrodes were:

| (electrode controlled = electrode at which temperature was controlled) | | | | | |
|---|---|---|---|---|---|
| Length of each electrode in needle | Uni or Bi | Electrode controlled | Temp of P electrode | Temp of D electrode | p value |
| P = 1 mm, D = 1 mm | Bi | P(1 mm) | 82 ± 1 | 82 ± 2 | 0.7 |
| P = 1 mm, D = 1 mm | Uni | P(1 mm) | 83 ± 1 | 82 ± 2 | 0.01 |
| P = 1 mm, D = 1.5 mm | Bi | P(1 mm) | 81 ± 1 | 60 ± 1 | <0.001 |
| P = 1 mm, D = 1.5 mm | Bi | D(1.5 mm) | 96 ± 2 | 80 ± 2 | <0.001 |
| P = 1 mm, D = 1.5 mm | Uni | Both | 82 ± 2 | 81 ± 1 | 0.24 |

Simultaneous multi-electrode ablation without closed-loop temperature control of each electrode results in higher temperature at the smaller electrode-tissue interface and lower temperature at the larger electrode-tissue interface. This results in varying lesion sizes and potentially coagulum formation and impedance rises. Unipolar RF ablation with simultaneous closed-loop temperature control of each electrode is the optimum method for simultaneous multi-electrode ablation.

Second Embodiment

Figure 4:
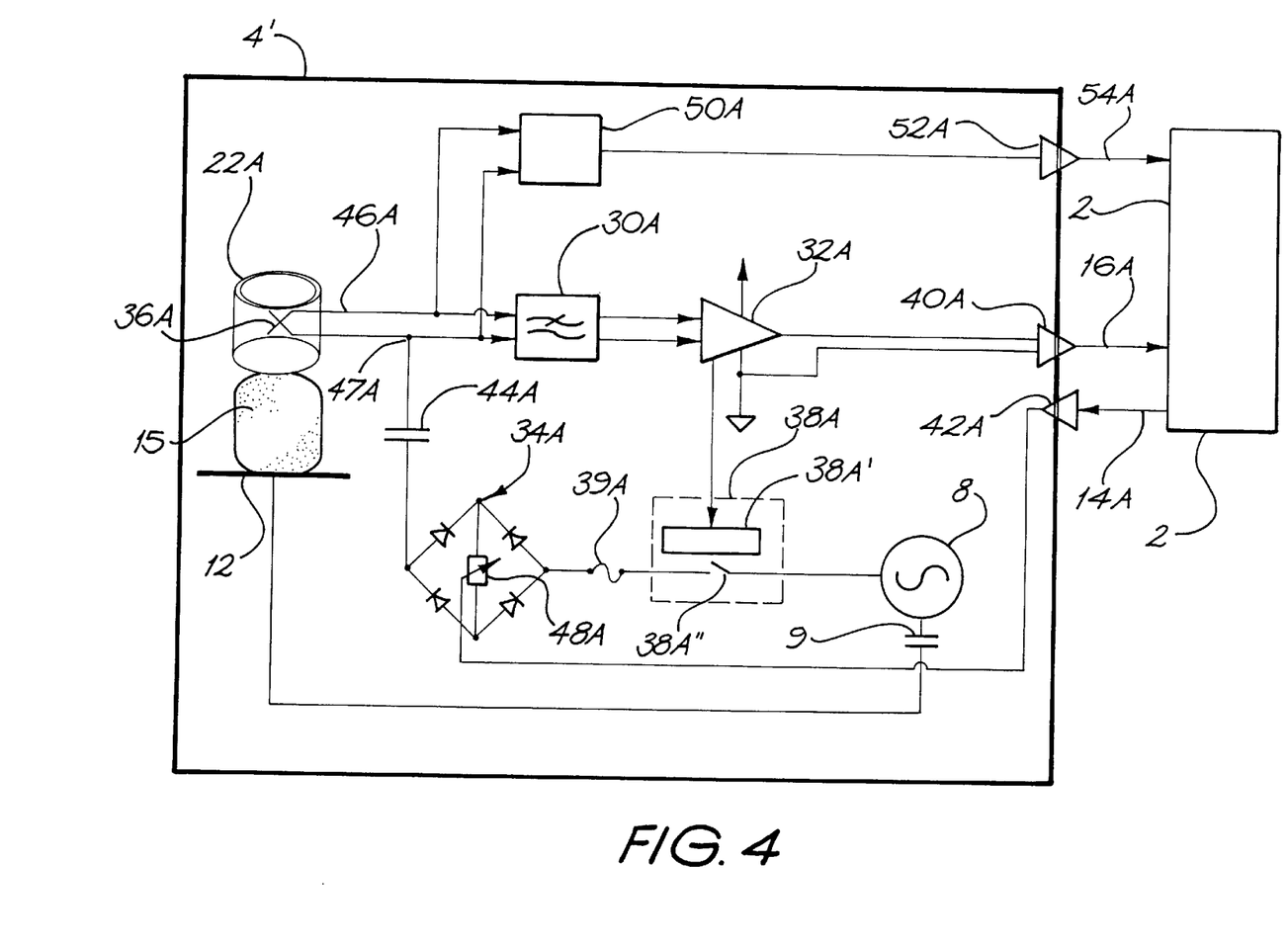
FIG. 4 is a detailed schematic of a single channel of an RF ablation system according to another embodiment.

Another embodiment of the invention is illustrated in FIG. 4, in which like elements of FIGS. 1 to 3 are indicated with the same reference numerals, For the purpose of brevity only, components of the second embodiment shared with the first embodiment are not repeated hereinafter. However, those aspects of the second embodiment will be readily understood by a person skilled in the art in view of the description with reference to FIGS. 1 to 3. Instead, the description hereinafter describes those aspects of the second embodiment not set forth above.

A single channel of the system according to the second embodiment is shown schematically in FIG. 4. The system comprises the programmable controller 2 and the module 4', which comprises the like numbered elements of FIG. 2, a voltage/current sensing module 50A and the corresponding isolation amplifier 52A. Again, while the RF generator 8 is illustrated within the module 4', it will be apparent to a person skilled in the art that the RF generator 8 can be equally applied to plural channels, as indicated in FIG. 3.

The conductors 46A and 47A are also coupled to the input terminals of the voltage and/or current sensing module 50A, which preferably detects the root-mean-square (RMS) voltage and/or current at the electrode 22A. The detected or measured voltage and/or current signal is output by the sensing module 50A and provided to isolation amplifier 52A. In urn the output of the isolation amplifier 52A is provided to the programmable controller 2.

The voltage and/or current sensing module 50A measures the RMS voltage and current delivered to the electrode 22A Thus, the average power and impedance of each electrode 22A can be determined independently as well. Thus, the module 50A independently senses at least one of following: the voltage, current, impedance and average power of each electrode. This is done to provide a corresponding measurement signal which can be used by the programmable controller so that additional safety features may be implemented in the system. This preferably provides an increased level of safety by enabling predetermined cut-off levels (eg, RMS voltage, RMS current, impedance and average power) to be used to shut-down the output of each electrode 22A. This is preferably carried out by the programmable controller 2 which provides control signal 14A dependent upon at least one of these criteria. Thus, the controller 2 generates the control signal 14A to independently interrupt delivery of the RF energy to the respective electrode when the meaurement signal exceeds a predetermined threshold condition. Further control structures utilising RMS voltage and/or current may also be applied to enhance the control and safety performance of the system.

Thus, the second embodiment provides, in addition to the advantages of the first embodiment, additional safety features.

While only a small number of embodiments of the invention has been described, it will be apparent to a person skilled in the art that modifications and chances thereto can be made without departing from the scope and spirit of the present invention.

What is claimed is:

1. A system for ablating tissues, comprising:
   means for generating RF energy;
   a probe comprising N separate electrodes, each one of the electrodes having a corresponding means for sensing the temperature of said one of the electrodes;
   splitter means for splitting said RF energy from said generating means to said electrodes, said splitter means having N separate channels respectively coupled to said N electrodes; and
   means for independently controlling said splitter means for independently controlling an individual temperature and thereby ablation of tissue at each of said electrodes by using closed loop feedback of the temperature sensed of each of said electrodes by independently regulating the amount of said RF energy to each of said electrodes individually.

2. The system according to claim 1, comprising a plurality of probes and splitter means, wherein said controlling means separately controls each of said probes and said corresponding splitter means.

3. The system according to claim 1, wherein said probe means has an elongated needle-like structure with one end adapted to puncture tissue and having sufficient rigidity to puncture said tissue, wherein each of said electrodes consists of a metal substantially circular surface separated one from another by insulation .

4. The system according to claim 1, wherein said probe is a catheter probe device.

5. The system according to claim 1, wherein said RF energy has a single phase.

6. The system according to claim 1, further comprising means for independently and continuously adjusting said RF energy delivered to each electrode in response to a control signal from said controlling means dependent on said temperature of said electrode.

7. The system according to claim 1, wherein said controlling means is programmable.

8. The system according to claim 1, wherein each respective temperature sensing means comprises a thermocouple.

9. The system according to claim 1, wherein said splitter means comprises means for independently interrupting current from said RF energy generating means to one or more of said electrodes.

10. The system according to claim 1, further comprising means for independently sensing at least one of the group consisting of the voltage, current, impedance and average power of each electrode to provide a corresponding measurement signal; and
wherein said controlling means generates said control signal to independently interrupt delivery of said RF energy to said respective electrode when said meaurement signal exceeds a predetermined threshold condition.

11. A medical apparatus for treatment by radiofrequency (RF) ablation of tissue, said apparatus comprising;
an RF energy generator;
one or more probes each comprising a plurality of separate electrodes and corresponding temperature sensors for sensing the temperature of each of said electrodes, each of said temperature sensors being connected to a respective one of said electrodes;
a splitter for splitting RF energy of said RF energy generator, said splitter having a plurality of separate channels, wherein each of said electrodes is coupled to a respective one of said channels; and
a programmable controller coupled to said splitter for independently controlling an individual temperature and thereby ablation of tissue at each of said electrodes using closed loop feedback of the sensed temperature of each of said electrodes wherein the amount of said RF energy coupled to each of said electrodes is independently regulated by said programmable controller individually.

12. The medical apparatus according to claim 11, comprising at least two probes, and wherein said programmable controller separately controls each of said probes.

13. The medical apparatus according to claim 11, wherein each probe has an elongated needle-like structure with one end adapted to puncture tissue and having sufficient rigidity to puncture said tissue, wherein each of said electrodes consists of metal separated one from another by insulative material.

14. The medical apparatus according to claim 11 wherein said RF energy has a single phase.

15. The medical apparatus according to claim 11, further comprising means for independently and continuously adjusting said RF energy delivered to each electrode in response to said programmable controller dependent on said temperature of said electrode.

16. The medical apparatus according to claim 11 wherein each probe is a catheter device.

17. The medical apparatus according to claim 11, wherein each of said temperature sensors comprises a temperature transducer.

18. The medical apparatus according to claim 17 wherein said temperature transducer is a thermocouple at least partially embedded in said respective electrode.

19. The medical apparatus according to claim 11 wherein each channel of said splitter is coupled to means for interrupting current delivered to the corresponding electrode.

20. The medical apparatus according to claim 11 comprising means for independently interrupting the delivery of RF energy to each electrode when at least one of the voltage, current, impedance and average power measured at the respective electrode exceeds a predetermined threshold.

21. A method for ablating tissue, comprising the steps of:
generating RF energy;
providing a probe comprising N separate electrodes, each one of said electrodes having a corresponding means for sensing temperature of said one of said electrodes;
sensing the temperature of each of said electrodes using said temperature sensing means of said electrodes;
splitting said RF energy to said probe into N separate channels each being coupled to a corresponding one of said N electrodes; and
independently controlling the splitting of said RF energy to said electrodes for independently controlling an individual temperature and thereby ablation of tissue at each of said electrodes using closed loop feedback of the measured temperature of each of said electrodes independently by independently regulating the amount of said RF energy delivered to each of said electrodes.

22. The method according to claim 21, further comprising the step of separately controlling the splitting of said RF energy to a plurality of said probe.

23. The method according to claim 21, wherein said probe has an elongated needle-like structure with one end adapted to puncture tissue and having sufficient rigidity to puncture said tissue; wherein each of said electrodes consists of a metal substantially circular surface separated one from another by insulation.

24. The method according to claim 21 wherein said RF energy has a single phase.

25. The method according to claim 21, further comprising the step of independently and continuously adjusting said RF energy delivered to each electrode in response to a control signal from a programmable controlling means dependent on said temperature of said electrode.

26. The method according to claim 21, further comprising the steps of:
sensing at least one of the group consisting of the voltage, current, impedance and average power of the respective electrode; and
independently interrupting the delivery of said RF energy to said electrode if a predetermined threshold is exceeded by the sensed value.

27. A method for treatment by radiofrequency (RF) ablation of tissue, said method comprising the steps of:
generating RF energy;
providing one or more probes each comprising a plurality of separate electrodes and corresponding temperature sensors, each one of said temperature sensors being connected to a respective one of said electrodes;
measuring the temperature of each of said electrodes using said respective one of said temperature sensors;
splitting said RF energy into a plurality of separate channels, wherein each of said electrodes is coupled to a respective one of said plurality of channels; and
programmably controlling the splitting of said RF energy so as to independently control an individual temperature and thereby ablation of tissue at each of said electrodes using closed loop feedback of the measured temperature of each of said electrodes wherein the amount of said RF energy coupled to each of said electrodes is independently regulated.

28. The method according to claim 27, comprising the further steps of using at least two probes, and programmably controlling each of said probes separately.

29. The method according to claim 27, wherein each probe has an elongated needle-like structure with one end adapted to puncture tissue and having sufficient rigidity to puncture said tissue, wherein each of said electrodes consists of metal separated one from another by insulative material.

30. The method according to claim 27, wherein said RF energy has a single phase.

31. The method according to claim 27, further comprising the step of independently and continuously adjusting said RF energy delivered to each electrode in response to said temperature of said eletrode.

32. The method according to claim 27, further comprising the step of independently interrupting the delivery of RF energy to each electrode when at least one of the voltage, current, impedance and average power measurement at the respective electrode exceeds a predetermined threshold.

* * * * *